United States Patent
Nakama et al.

(10) Patent No.: US 12,330,974 B2
(45) Date of Patent: Jun. 17, 2025

(54) WATER SUPPLY SYSTEM FOR AIRCRAFT

(71) Applicant: NIKKISO CO., LTD., Tokyo (JP)

(72) Inventors: Takahiro Nakama, Tokyo (JP); Takahiro Akutsu, Tokyo (JP); Satoko Takigawa, Tokyo (JP)

(73) Assignee: Nikkiso Co., Ltd., Tokyo (JP)

(*) Notice: Subject to any disclaimer, the term of this patent is extended or adjusted under 35 U.S.C. 154(b) by 425 days.

(21) Appl. No.: 17/414,710

(22) PCT Filed: Dec. 6, 2019

(86) PCT No.: PCT/JP2019/047884
§ 371 (c)(1),
(2) Date: Jun. 16, 2021

(87) PCT Pub. No.: WO2020/129711
PCT Pub. Date: Jun. 25, 2020

(65) Prior Publication Data
US 2022/0064039 A1    Mar. 3, 2022

(30) Foreign Application Priority Data

Dec. 17, 2018 (JP) .................. 2018-235300

(51) Int. Cl.
*C02F 9/00* (2023.01)
*A61L 2/10* (2006.01)
(Continued)

(52) U.S. Cl.
CPC ............ *C02F 9/00* (2013.01); *A61L 2/10* (2013.01); *A61L 2/183* (2013.01); *A61L 2/26* (2013.01);
(Continued)

(58) Field of Classification Search
None
See application file for complete search history.

(56) References Cited

U.S. PATENT DOCUMENTS

| 4,871,452 A | 10/1989 | Kohler et al. |
| 7,413,650 B2* | 8/2008 | Lumbert ............. C02F 1/78 |
| | | 210/178 |

(Continued)

FOREIGN PATENT DOCUMENTS

| DE | 10 2013 103 517 A1 | 10/2014 |
| JP | H6-67299 U | 9/1994 |

(Continued)

OTHER PUBLICATIONS

Translation of International Preliminary Report on Patentability and Written Opinion dated Jul. 1, 2021 issued in PCT/JP2019/047884.
(Continued)

*Primary Examiner* — Krishnan S Menon
(74) *Attorney, Agent, or Firm* — Scully, Scott, Murphy & Presser, PC

(57) ABSTRACT

A water supply system for aircraft that is mounted on an aircraft to supply water to a plurality of water supply outlets in the aircraft. The water supply system for aircraft includes a tank for storing water, a water supply pipe, and an ultraviolet sterilization device. The water supply pipe extends from the tank, branches and is connected to each of the plurality of water supply outlets, and supplies water from the tank to the plurality of water supply outlets. The ultraviolet sterilization device is provided on the water supply pipe close to at least the water supply outlet for drinking water, includes a light-emitting diode emitting ultraviolet light, and sterilizes water supplied to the water supply outlet by irradiating the water with ultraviolet light from the light-emitting diode.

7 Claims, 3 Drawing Sheets

(51) Int. Cl.
*A61L 2/18* (2006.01)
*A61L 2/26* (2006.01)
*A61L 101/02* (2006.01)
*B64D 11/02* (2006.01)
*C02F 1/00* (2023.01)
*C02F 1/32* (2023.01)
*C02F 1/78* (2023.01)

(52) U.S. Cl.
CPC .............. *B64D 11/02* (2013.01); *C02F 1/006* (2013.01); *A61L 2101/02* (2020.08); *A61L 2202/11* (2013.01); *A61L 2202/17* (2013.01); *C02F 1/001* (2013.01); *C02F 1/325* (2013.01); *C02F 1/78* (2013.01); *C02F 2201/009* (2013.01); *C02F 2201/3222* (2013.01); *C02F 2201/3227* (2013.01); *C02F 2201/3228* (2013.01); *C02F 2201/782* (2013.01); *C02F 2303/04* (2013.01)

(56) References Cited

U.S. PATENT DOCUMENTS

| | | | |
|---|---|---|---|
| 7,666,317 B2 | 2/2010 | Hsueh et al. | |
| 9,061,923 B2 | 6/2015 | Hsueh et al. | |
| 9,346,687 B1* | 5/2016 | Matthews | C02F 1/325 |
| 10,662,627 B2 | 5/2020 | Hills et al. | |
| 2005/0000911 A1* | 1/2005 | Thorpe | C02F 1/325 |
| | | | 210/748.12 |
| 2006/0157425 A1* | 7/2006 | Rice | C02F 9/00 |
| | | | 210/748.11 |
| 2006/0169645 A1 | 8/2006 | Hsueh | |
| 2006/0169649 A1 | 8/2006 | Hsueh et al. | |
| 2008/0136191 A1* | 6/2008 | Baarman | F03B 3/04 |
| | | | 290/54 |
| 2010/0059455 A1 | 3/2010 | Hsueh et al. | |
| 2010/0314551 A1 | 12/2010 | Bettles et al. | |
| 2011/0180618 A1 | 7/2011 | Schumacher et al. | |
| 2013/0175452 A1 | 7/2013 | Hsueh et al. | |
| 2014/0166566 A1 | 6/2014 | Schreiner et al. | |
| 2014/0352799 A1* | 12/2014 | Rosko | C02F 1/78 |
| | | | 137/237 |
| 2016/0229703 A1 | 8/2016 | Nolan | |
| 2018/0051447 A1 | 2/2018 | Hills et al. | |
| 2018/0207302 A1 | 7/2018 | Vasilenko | |

FOREIGN PATENT DOCUMENTS

| | | |
|---|---|---|
| JP | 2005-2570 A | 1/2005 |
| JP | 2007-31983 A | 2/2007 |
| JP | 2008-528275 A | 7/2008 |
| JP | 2018-69224 A | 5/2018 |
| WO | 2010/058187 A2 | 5/2010 |

OTHER PUBLICATIONS

Extended European Search Report dated Aug. 17, 2022 from related EP 19899893.2.
Official Action dated Sep. 13, 2022 received from the Japanese Patent Office in related JP 2018-235300 together with English language translation.
International Search Report dated Jan. 7, 2020 issued in PCT/JP2019/047884.
Office Action dated Feb. 22, 2024 from related EP 19899893.2.

* cited by examiner

WATER SUPPLY SYSTEM FOR AIRCRAFT

TECHNICAL FIELD

The invention relates to a water supply system for aircraft.

BACKGROUND ART

In aircrafts, water stored in a dedicated tank is used as drinking water, etc. Pressure in the tank is increased by introducing compressed air taken from an aircraft engine, etc., or compressed air from an air pump, into the tank and water in the tank is thereby sent to predetermined supply outlets (faucets, etc.).

Patent Document 1 can be found as prior art document information related to the invention of the present application.

CITATION LIST

Patent Literature

Patent Document 1: Japanese Translation of PCT International Application Publication No. 2008-528275

SUMMARY OF INVENTION

Technical Problem

In aircraft water supply systems, tanks and water supply pipes are cleaned with chemicals, etc., to suppress growth of bacteria, etc., in the tanks and water supply pipes. However, sterilization performed by cleaning is not sufficient and very low-quality water is used as drinking water under the current circumstances.

Particularly with aircrafts, water in the tank is sometimes used as it is in the return flight without being replaced because the water in the tank cannot be discharged in a cold district, etc., and the quality of water stored for a long time is never high.

An aircraft water supply system having a filter in a water supply pipe has been proposed. However, bacteria collected by the filter could grow in the filter, hence, improvement is desired.

Therefore, it is an object of the invention to provide a water supply system for aircraft that is capable of improving the quality of water supplied in an aircraft.

Solution to Problem

To solve the above-described problem, the invention provides a water supply system for aircraft that is mounted on an aircraft to supply water to a plurality of water supply outlets in the aircraft, the water supply system for aircraft comprising: a tank for storing water; a water supply pipe extending from the tank, branching and being connected to each of the plurality of water supply outlets, and supplying water from the tank to the plurality of water supply outlets; and an ultraviolet sterilization device provided on the water supply pipe close to at least the water supply outlet for drinking water, comprising a light-emitting diode emitting ultraviolet light, and sterilizing water supplied to the water supply outlet by irradiating the water with ultraviolet light from the light-emitting diode.

Advantageous Effects of Invention

According to the invention, it is possible to provide a water supply system for aircraft that is capable of improving the quality of water supplied in an aircraft.

DESCRIPTION OF EMBODIMENT

[Embodiment]

An embodiment of the invention will be described below in conjunction with the appended drawings.

Figure 1:
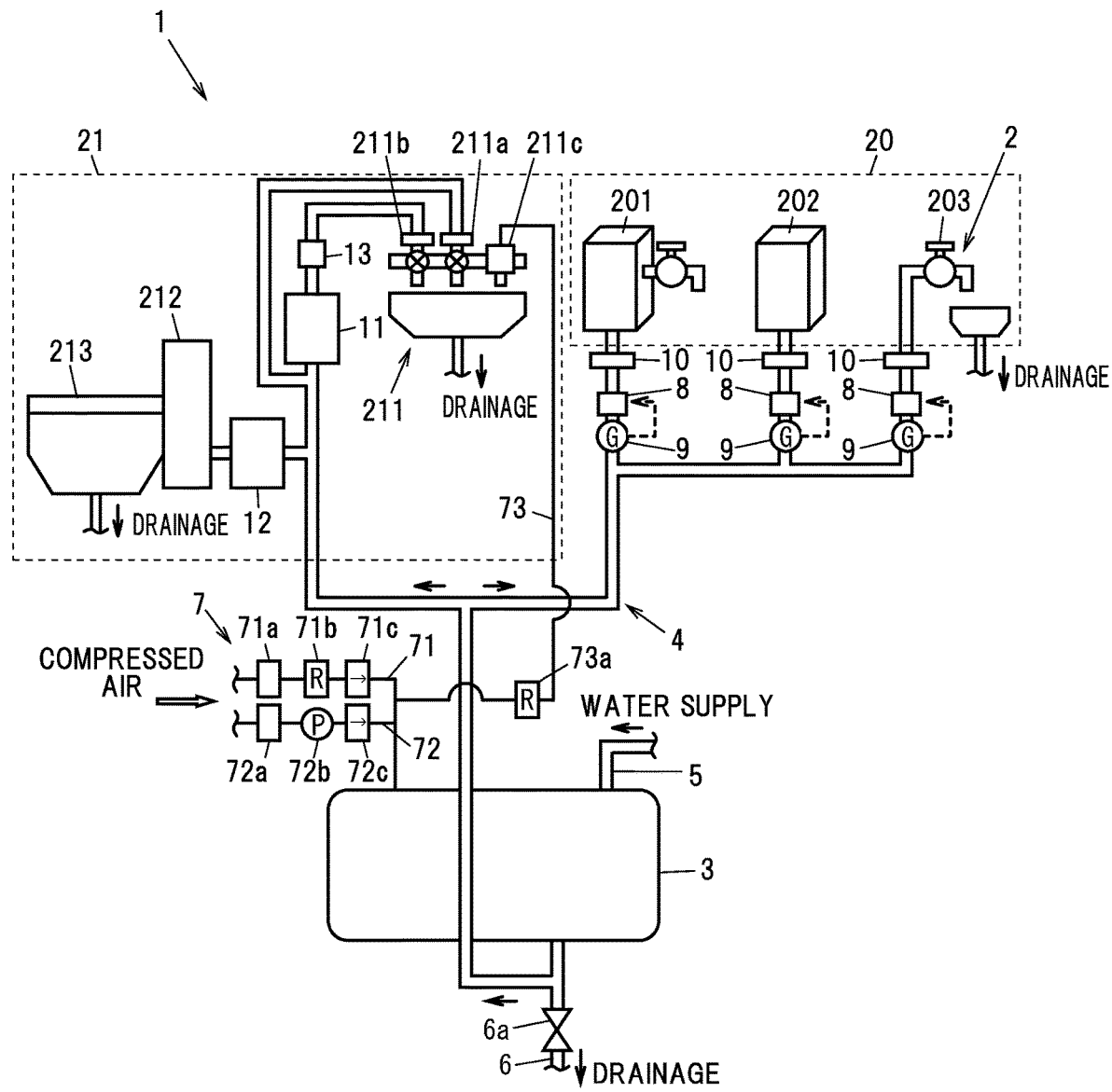
FIG. 1 is a schematic configuration diagram illustrating a water supply system for aircraft in an embodiment of the present invention.

FIG. 1 is a schematic configuration diagram illustrating a water supply system for aircraft in the present embodiment. As shown in FIG. 1, a water supply system 1 for aircraft is a system that is mounted on an aircraft to supply water to plural water supply outlets 2 in the aircraft.

The water supply system 1 for aircraft includes a tank 3 for storing water, and a water supply pipe 4 that extends from the tank 3, branches and is connected to each of the plural water supply outlets 2 and supplies water from the tank 3 to the plural water supply outlets 2.

The tank 3 is a large-size water storage tank storing water, and is also called a water tank or a portable water tank. A refilling pipe 5 for supplying water from the outside of the aircraft to the tank 3 is connected to the tank 3. A drainage pipe 6 is also connected in such a manner that it branches off the water supply pipe 4 extending out of the tank 3. A drain valve 6a which is opened at the time of drainage is provided on the drainage pipe 6.

One end of the water supply pipe 4 is connected to the tank 3 and the other end branches and is connected to each of the water supply outlets 2. In the example described here, the water supply outlets 2 have a water heater 201, a coffee maker 202 and a faucet 203 in a cooking cabinet (galley) 20 and a sink 211 and a toilet bowl cleaning tank 212 in a toilet 21. However, the water supply outlet 2 is not limited to that shown in the drawing and can be appropriately changed.

A compressed air introduction line 7 for introducing compressed air into the tank 3 is also connected to the tank 3. The compressed air introduction line 7 has a first line 71 for introducing compressed air from an engine or auxiliary engine of the aircraft, and a second line 72 for guiding outside air, which is compressed by an air pump 72b, into the tank 3. An air filter 71a, a pressure regulator 71b and a check valve 71c are provided on the first line 71. An air filter 72a, the air pump 72b and a check valve 72c are provided on the second line 72. Pressure in the tank 3 is increased by compressed air introduced from the compressed air introduction line 7 and water in the tank 3 is thereby supplied to each water supply outlet 2.

The water supply system 1 for aircraft in the present embodiment includes ultraviolet sterilization devices 8 provided on the water supply pipe 4 respectively close to at least the water supply outlets 2 for drinking water. The ultraviolet sterilization device 8 has light-emitting diodes 81 emitting ultraviolet light (see FIG. 2), and sterilizes water supplied to the water supply outlets by irradiating the water with ultraviolet light from the light-emitting diodes 81. Sterilization here also includes suppression of bacterial growth by inactivating bacteria.

In the present embodiment, the ultraviolet sterilization devices 8 are provided at portions of the water supply pipe 4 respectively connected to the water heater 201, the coffee maker 202 and the faucet 203 in the cooking cabinet 20. In this regard, however, when the branching points of the water supply pipe 4 are close to the water supply outlets 2, one ultraviolet sterilization device 8 may be provided for plural water supply outlets 2.

Figure 2:
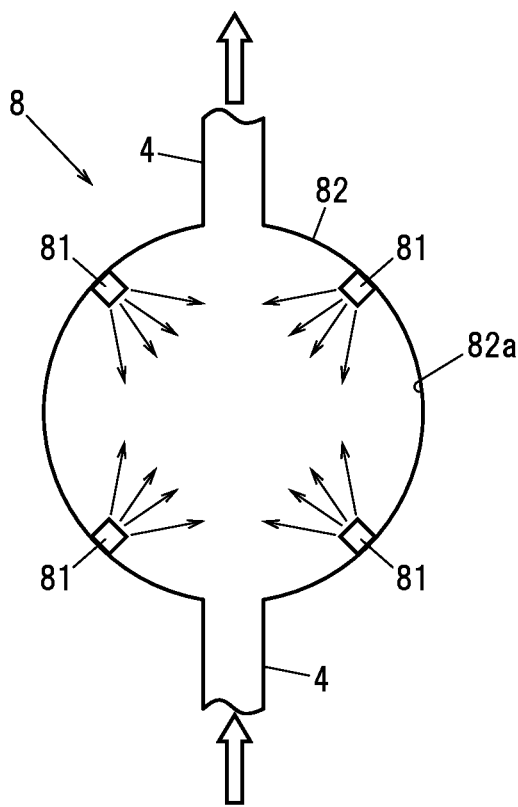
FIG. 2 is a schematic configuration diagram illustrating an example of an ultraviolet sterilization device.

As shown in FIG. 2, the ultraviolet sterilization device 8 has a spherical chamber 82 as a sterilization flow path inserted to the water supply pipe 4 and sterilizes water by irradiating water in the chamber 82 with ultraviolet light from the light-emitting diode 81. An inner peripheral surface 82a of the chamber 82 is preferably made of a material that reflects ultraviolet light, and it is desirable to improve efficiency of water sterilization by causing multiple reflection of ultraviolet light in the chamber 82. To avoid recontamination by bacteria, etc., after sterilization, it is desirable to arrange the ultraviolet sterilization devices 8 as close to the water supply outlets 2 as possible. The specific configuration of the ultraviolet sterilization device 8 is not limited to the configuration shown in FIG. 2.

The light-emitting diode 81 used for the ultraviolet sterilization device 8 preferably emits ultraviolet light with a wavelength of not less than 250 nm and not more than 350 nm. That is, it is desirable to use the light-emitting diode 81 of which center wavelength or peak wavelength is included in the range of not less than 250 nm and not more than 350 nm. To further improve the sterilization effect, it is more desirable to use the light-emitting diode 81 that emits ultraviolet light with a wavelength of not less than 255 nm and not more than 285 nm which has a high bactericidal effect.

In this regard, for example, a device for performing sterilization by irradiating water in the tank 3 with ultraviolet light could be provided in the tank 3, but in this case, contamination by bacteria in the water supply pipe 4 is not avoided. By providing the ultraviolet sterilization devices 8 on the water supply pipe 4 close to the water supply outlets 2 as in the present embodiment, it is possible to kill (or inactivate) bacteria contaminating the tank 3 or the water supply pipe 4 and thereby possible to improve the quality of water supplied through the water supply outlets 2.

Returning back to FIG. 1, in the present embodiment, a small running water power generator 9 which generates power using water flowing through the water supply pipe 4 is provided close to each ultraviolet sterilization device 8. Each ultraviolet sterilization device 8 is driven using power generated by the corresponding running water power generator 9. The ultraviolet sterilization device 8 may alternatively be driven using power generated by the running water power generator 9 and another power. As a result, it is possible to suppress power consumption of the ultraviolet sterilization device 8 and the running cost is reduced.

In addition, in the present embodiment, a filter 10 for filtering water is provided on the downstream side of each ultraviolet sterilization device 8. For example, if the filter 10 is provided on the upstream side of the ultraviolet sterilization device 8, the bacteria collected by the filter 10 could grow in the filter 10, causing a decrease in the quality of water. In contrast, since the filter 10 is provided on the downstream side of each ultraviolet sterilization device 8 in the present embodiment, it is possible to suppress growth of bacteria in the filter 10.

In the water supply system 1 for aircraft in the present embodiment, a water supply faucet 211a, a sterilized water supply outlet 211b for supplying ozone water and a hand dryer 211c are provided at the sink 211 in the toilet 21. The faucet 211a and the sterilized water supply outlet 211b are respectively connected to branches of the water supply pipe 4.

Figure 3:
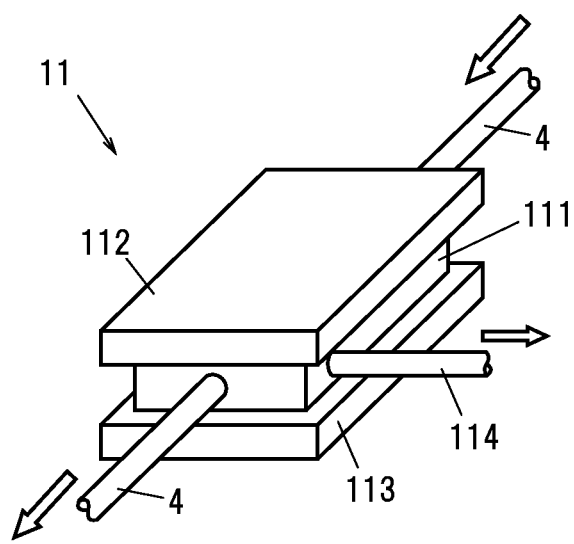
FIG. 3 is a schematic configuration diagram illustrating an example of an ozone water generator.

An ozone water generator 11 for generating and supplying ozone water to the sterilized water supply outlet 211b is provided on the water supply pipe 4 close to the sterilized water supply outlet 211b. As shown in FIG. 3, the ozone water generator 11 has a rectangular parallelepiped-shaped chamber 111 inserted to the water supply pipe 4, and plate-shaped anode and cathode electrodes 112 and 113 provided so as to sandwich the chamber 111. The water in the chamber 111 is electrolyzed by applying a voltage between the two electrodes 112, 113 and ozone water is thereby generated. A cathode water discharge flow path 114 is connected to the chamber 111 to discharge cathode water that is generated in the chamber 111 and contains a large amount of hydrogen. The specific configuration of the ozone water generator 11 is not limited to the configuration shown in FIG. 3.

An ozone concentration meter 13 for measuring an ozone concentration in the ozone water generated by the ozone water generator 11 is provided on the downstream side of the ozone water generator 11. As the ozone concentration meter 13, it is possible to use an ultraviolet light absorbing-type ozone concentration meter that uses a light-emitting diode emitting ultraviolet light. A running water power generator that generates power using water flowing through the water supply pipe 4 may be provided to drive the ozone water generator 11 or the ozone concentration meter 13.

In aircrafts, part of drainage water is discharged from a drain mast to the outside, but wastewater from toilets, etc., is stored in a waste tank. Drainage water from the sink 211 is also stored in the waste tank. However, when soap is used in the sink 211, the waste tank becomes sudsy and it makes post-treatment awkward. For this reason, less lathering soap is generally used in the sink 211 under the current circumstances, but it is difficult to obtain a sufficient sterilization effect only by such a measure. By enabling handwashing with ozone water at the sink 211 as in the present embodiment, it is possible to obtain a sufficient sterilization effect. In addition, since the ozone water is collected into the waste tank, it is also possible to sterilize the waste tank.

The compressed air introduction line 7 (the first line 71 and the second line 72) is connected to the hand dryer 211c via a dryer connection line 73, and it is configured that compressed air from the compressed air introduction line 7 is blown out of the hand dryer 211c. A pressure regulator 73a for regulating pressure of air blown out of the hand dryer 211c is provided on the dryer connection line 73. By configuring so that the hand dryer 211c uses compressed air from the compressed air introduction line 7, the necessity of driving a fan as in the conventional technique is eliminated and it is possible to reduce power consumption.

Figure 4:
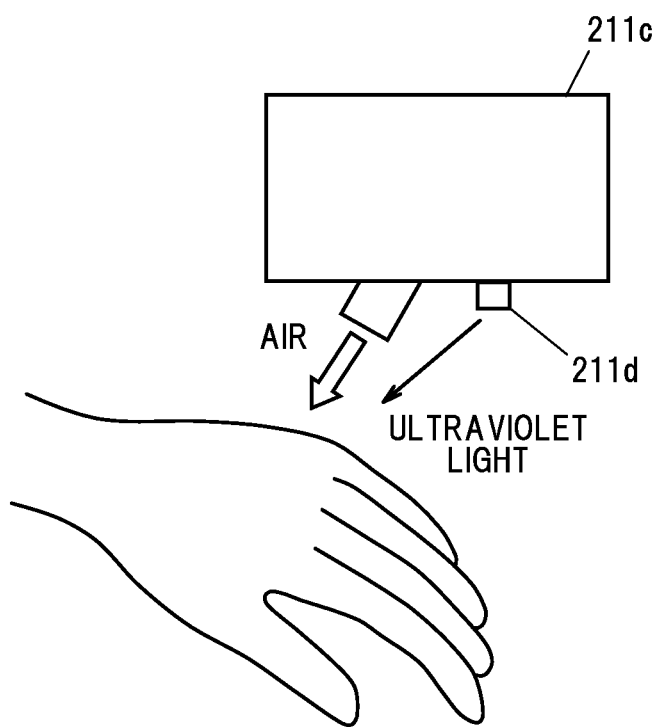
FIG. 4 is a schematic configuration diagram illustrating a hand dryer.

Additionally, an ultraviolet light emitter 211d for emitting ultraviolet light onto user's hands to be dried may be provided on the hand dryer 211c, as shown in FIG. 4. As a light source used for the ultraviolet light emitter 211d, it is desirable to use a light-emitting diode that is low in power consumption. When ozone water is irradiated with ultraviolet light, hydroxy radicals with a powerful oxidizing action are produced and the sterilization effect is improved by enhanced oxidation. Therefore, it is possible to provide handwashing with higher sterilization effect to passengers by combining the ozone water supply with the hand dryer 211c having the ultraviolet light emitter 211d.

Furthermore, in the present embodiment, it is configured that the ozone water is also used in the toilet bowl cleaning tank 212 used for cleaning the toilet bowl in the toilet. In this regard, the toilet bowl cleaning tank 212 is used to store water for flushing a toilet bowl 213.

In the present embodiment, an ozone water generator 12 for generating and supplying ozone water to the toilet bowl cleaning tank 212 is provided on the water supply pipe 4 close to the toilet bowl cleaning tank 212. However, it is not limited thereto, and an ozone water generator may be provided in the toilet bowl cleaning tank 212. The detailed description of the ozone water generator 12 will be omitted since it has the same structure as the ozone water generator 11 described in reference to FIG. 3. Although the separate ozone water generators 11 and 12 are used for supplying ozone water to the sterilized water supply outlet 211b and for supplying ozone water to the toilet bowl cleaning tank 212 in the present embodiment, it may be configured such that ozone water generated by one ozone water generator 11 or 12 is supplied to both the sterilized water supply outlet 211b and the toilet bowl cleaning tank 212.

By configuring to clean the toilet bowl 213 with ozone water stored in the toilet bowl cleaning tank 212, the toilet bowl 213 can be sterilized every time water is flushed, and it is thus possible to suppress occurrence of airborne bacteria from the toilet bowl 213.

(Functions and Effects of the Embodiment)

As described above, the water supply system 1 for aircraft in the present embodiment includes the ultraviolet sterilization devices 8 provided on the water supply pipe 4 close to at least the water supply outlets 2 for drinking water, each having light-emitting diodes emitting ultraviolet light, and sterilizing water supplied to the water supply outlets 2 by irradiating the water with ultraviolet light from the light-emitting diodes.

By using the ultraviolet sterilization devices 8, it is possible to kill (or inactivate) bacteria contaminating water supplied through the water supply outlets 2 and it is thereby possible to improve the quality of water supplied in the aircraft. The ultraviolet sterilization device 8 using the light-emitting diodes is smaller in size and consumes less power than, e.g., a sterilization device using an ultraviolet lamp, etc. Therefore, even in an aircraft having a limited arrangement space, the ultraviolet sterilization device 8 can be easily installed and can be used without power source when, e.g., combined with the running water power generator 9.

(Summary of the Embodiment)

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A water supply system (1) for aircraft that is mounted on an aircraft to supply water to a plurality of water supply outlets (2) in the aircraft, the water supply system (1) for aircraft comprising: a tank (3) for storing water; a water supply pipe (4) extending from the tank (3), branching and being connected to each of the plurality of water supply outlets (2), and supplying water from the tank (3) to the plurality of water supply outlets (2); and an ultraviolet sterilization device (8) provided on the water supply pipe (4) close to at least the water supply outlet (2) for drinking water, comprising a light-emitting diode emitting ultraviolet light, and sterilizing water supplied to the water supply outlet (2) by irradiating the water with ultraviolet light from the light-emitting diode.

[2] The water supply system (1) for aircraft described in [1], comprising: a running water power generator (9) that generates power using water flowing through the water supply pipe (4), wherein the ultraviolet sterilization device (8) is driven using power generated by the running water power generator (9).

[3] The water supply system (1) for aircraft described in [1] or [2], wherein a filter (10) for filtering the water is provided on the downstream side of the ultraviolet sterilization device (8).

[4] The water supply system (1) for aircraft described in any one of [1] to [3], wherein the water supply outlets (2) comprise a sterilized water supply outlet (211b) provided at a sink (211), and an ozone water generator (11) for generating and supplying ozone water to the sterilized water supply outlet (211b) is provided on the water supply pipe (4) close to the sterilized water supply outlet (211b).

[5] The water supply system (1) for aircraft described in any one of [1] to [4], wherein the water supply outlets (2) comprise a toilet bowl cleaning tank (212) used for cleaning a toilet bowl in a toilet (21), and an ozone water generator (12) for generating and supplying ozone water to the toilet bowl cleaning tank (212) is provided on the water supply pipe (4) close to the toilet bowl cleaning tank (212), or provided in the toilet bowl cleaning tank (212).

Although the embodiment of the invention has been described, the invention according to claims is not to be limited to the embodiment described above. In addition, all combinations of the features described in the embodiment are not necessary to solve the problem of the invention. In addition, the invention can be appropriately modified and implemented without departing from the gist thereof.

REFERENCE SIGNS LIST

1: water supply system for aircraft
2: water supply outlet
3: tank
4: water supply pipe
8: ultraviolet sterilization device
9: running water power generator
10: filter
11, 12: ozone water generator
21: toilet
211: sink
211b: sterilized water supply outlet
211c: hand dryer
212: toilet bowl cleaning tank
213: toilet bowl

The invention claimed is:

1. A water supply system for aircraft that is mounted on an aircraft to supply water to a plurality of water supply outlets in the aircraft, the water supply system for aircraft comprising:
   a tank for storing water;
   a water supply pipe extending from the tank, branching and being connected for supplying water to each of a plurality of water supply outlets for drinking water, and being connected to each of a plurality of water supply outlets for washing hands;

an ultraviolet sterilization device provided in the water supply pipe downstream of the tank and located spaced from the at least one of the plurality of water supply outlets for drinking water, the ultraviolet sterilization device comprising:
  a chamber inserted in the water supply pipe;
  a filter for filtering the water provided on the downstream side of the ultraviolet sterilization device; and
  at least one light-emitting diode emitting ultraviolet light located inside the chamber, and sterilizing water supplied to the at least one water supply outlet for drinking water by irradiating the water with ultraviolet light from the at least one light-emitting diode; and an ozone water generator provided in the water supply pipe downstream of the tank for generating and supplying ozone concentrated water to the at least one water supply outlet for washing hands provided on the water supply pipe leading to the at least one water supply outlet for washing hands.

2. The water supply system for aircraft according to claim 1, comprising:
  a running water power generator that generates power using water flowing through the water supply pipe,
  wherein the ultraviolet sterilization device is driven using power generated by the running water power generator.

3. The water supply system for aircraft according to claim 1, wherein the at least one light-emitting diode is provided on an inner peripheral surface of the chamber.

4. The water supply system for aircraft according to claim 1, further comprising a compressed air line connected to the tank for introducing compressed air into the tank, wherein the compressed air line comprises a first line connected to an engine or auxiliary engine of the aircraft for introducing compressed air into the tank, and a second line including an air pump for introducing compressed outside air into the tank.

5. The water supply system for aircraft according to claim 3, wherein the ultraviolet sterilization device comprises a plurality of light-emitting diodes arranged on the inner surface of the chamber evenly spaced apart and to point towards the center of the chamber to cause multiple reflection from the inner surface made of material that reflects ultraviolet light.

6. A water supply system for aircraft that is mounted on an aircraft to supply water to a plurality of water supply outlets in the aircraft, the water supply system for aircraft comprising:
  a tank for storing water;
  a water supply pipe extending from the tank for storing water, branching and being connected for supplying water to each of a plurality of water supply outlets for drinking water, and being connected to a toilet bowl cleaning tank;
  an ultraviolet sterilization device provided in the water supply pipe downstream of the tank for storing water and located spaced from the at least one of the plurality of water supply outlets for drinking water, the ultraviolet sterilization device comprising:
    a chamber inserted in the water supply pipe;
    a filter for filtering the water provided on the downstream side of the ultraviolet sterilization device; and
    at least one light-emitting diode emitting ultraviolet light located inside the chamber, and sterilizing water supplied to the at least one water supply outlet for drinking water by irradiating the water with ultraviolet light from the at least one light-emitting diode; and
  an ozone water generator provided in the water supply pipe downstream of the tank for generating and supplying ozone concentrated water to the toilet bowl cleaning tank provided on the water supply pipe leading to the toilet bowl cleaning tank.

7. The water supply system for aircraft according to claim 1, further comprising an ozone meter provided downstream of the ozone water generator.

* * * * *